(12) United States Patent
Kommisrud et al.

(10) Patent No.: US 8,178,130 B2
(45) Date of Patent: May 15, 2012

(54) PRESERVATION AND CONTROLLED DELIVERY / RELEASE OF SPERMATOZOA

(76) Inventors: Elisabeth Kommisrud, Stange (NO); Peer Ola Hofmo, Hamar (NO); Geir Klinkenberg, Heimdal (NO)

( * ) Notice: Subject to any disclaimer, the term of this patent is extended or adjusted under 35 U.S.C. 154(b) by 581 days.

(21) Appl. No.: 12/305,654

(22) PCT Filed: Jul. 3, 2007

(86) PCT No.: PCT/NO2007/000256
§ 371 (c)(1), (2), (4) Date: Mar. 11, 2009

(87) PCT Pub. No.: WO2008/004890
PCT Pub. Date: Jan. 10, 2008

(65) Prior Publication Data
US 2010/0041941 A1 Feb. 18, 2010

Related U.S. Application Data

(60) Provisional application No. 60/807,716, filed on Jul. 19, 2006.

(30) Foreign Application Priority Data

Jul. 4, 2006 (GB) .................................. 0613288.0

(51) Int. Cl.
*A61K 35/52* (2006.01)
(52) U.S. Cl. ...................................................... 424/561
(58) Field of Classification Search .................. None
See application file for complete search history.

(56) References Cited

U.S. PATENT DOCUMENTS

| 5,912,005 | A | 6/1999 | Lanza et al. |
| 6,596,310 | B1 | 7/2003 | Chou et al. |
| 2004/0086842 | A1 | 5/2004 | Holt et al. |

FOREIGN PATENT DOCUMENTS

| EP | 0652015 | 5/1995 |
| EP | 0922451 | 6/1999 |
| GB | 1061336 | 3/1967 |
| NZ | 562945 | 11/2007 |
| WO | WO 95/19743 | 7/1995 |
| WO | WO 96/25848 | 8/1996 |
| WO | WO 98/23226 | 6/1998 |
| WO | WO 98/48622 | 11/1998 |
| WO | WO 2006/106400 | 10/2006 |

OTHER PUBLICATIONS

Cheetham et al., "Physical Studies on Cell Immobilization Using Calcium Alginate Gels", Biotechnology and Bioengineering, 1979, vol. XXI, pp. 2155-2168.*
FMC BioPolymer Brochure/Handbook on Alginates, obtained from < http://www.novamatrix.biz/Portals/novamatrix/Content/Docs/FMC%20Alginate%20Brochure.pdf > Downloaded Oct. 2011.*
Koch et al., "Alginate encapsulation of genetically engineered mammalian cells: comparison of production devices, methods and microcapsule characteristics", J. Microencapsulation, 2003, 20(3):303-316.*
M. Faustini et al.: "Boar spermatozoa encapsulated in barium alginate membranes: a microdensitometric evaluation of some enzymatic activities during storage at 18° C.", Theriogenology, Los Altos, CA, US, vol. 61, No. 1, Jan. 1, 2004, pp. 173-184, XP002402013.
M.L. Torre et al.: "Boar semen controlled delivery system: storage and in vitro spermatozoa release", Journal of controlled release, Elsevier Amsterdam, NL, vol. 85, No. 1-3, Dec. 13, 2002, pp. 83-89, XP004397768.
M.L. Torre et al.: "Calcium alginate capsules containing a hydrophilic polymer for the encapsulatilon of swine spermatozoa", Science Techniques et Pratiques STP Pharma Sciences, Paris, FR, vol. 8, No. 4, pp. 233-236, XP009073273, 1998.
M.L. Torre et al.: "Controlled release of swine semen encapsulated in calcium alginate beads", Biomaterials, Elsevier Science Publishers BV., Barking, GB, vol. 21, No. 14, Jul. 2000, pp. 1493-1498, XP004199070.
O. Smidsrød et al.: "Alginate as immobilization matrix for cells", Trends in Biotechnology, Elsevier Publications, Cambridge, GB, vol. 8, No. 3, Mar. 1, 1990, pp. 71-78, XP000095653.
W. Weber et al.: "Design of high-throughput-compatible protocols for microencapsulation, cryopreservation and release of bovine spermatozoa", Journal of Biotechnology, Elsevier Science Publishers, Amsterdam, NL, vol. 123, No. 2, May 17, 2008, pp. 155-163, XP005408297.

* cited by examiner

*Primary Examiner* — Suzanne M Noakes
(74) *Attorney, Agent, or Firm* — Christian D. Abel

(57) ABSTRACT

The present invention relates to biopolymer particles for preservation of spermatozoa, wherein the spermatozoa are embedded within the biopolymer particle. The present invention also regards a method for preservation, storage and controlled delivery/release of spermatozoa, and the use of the biopolymer particles according to the present invention in breeding.

23 Claims, 4 Drawing Sheets

A: Bovine spermatozoa

B: Boar spermatozoa

PRESERVATION AND CONTROLLED DELIVERY / RELEASE OF SPERMATOZOA

FIELD OF INVENTION

The present invention relates to biopolymer particles for preservation of spermatozoa. The present invention also relates to a method for preservation, storage and controlled delivery/release of spermatozoa, and the use of the biopolymer particles according to the present invention in breeding.

BACKGROUND OF INVENTION

Artificial insemination (AI) is a technique wherein spermatozoa are placed into an animal's uterus or cervix by artificial means rather than by natural copulation. It is widely used as a method of mating, and in breeding of animals to propagate desirable characteristics, particularly in the case of farm animals such as cattle, swine, sheep, poultry and horses, but also in case of pets such as pedigree dogs, aquatic animals or endangered species.

Usually spermatozoa is collected, extended and then preserved by e.g. cryopreservation. The use of cryopreservation techniques presupposes that the spermatozoa from the specific species of animal tolerate such treatment without resulting in too much deterioration of the spermatozoa quality, viability and fertilization capacity. The spermatozoa are then transported to the female's location either cryopreserved or freshly stored, which ever is suitable. It is vital that the spermatozoa are maintained viable until the time of insemination and for a sufficient period of time inside the female animal after insemination until the egg cell(s) reach the location of fertilization.

Artificial insemination of farm animals has been used since the 1940s and is now widely used in the agriculture industry, especially for breeding dairy cattle and swine. An overview over the development of modern AI and the challenges of the breeders as regards the use of artificial insemination and preservation of spermatozoa is disclosed in R. H. Foote (2002), American Society of Animal Science (http://www.asas.org/symposia/esupp2/Footehist.pdf) and in "Reproduction in farm animals", edited by B. Hafez, E. S. E. Hafez.—7th ed., Philadelphia, Lippincott Williams & Wilkins, 2000.—XIII, ISBN 0-683-30577-8 (ib.). Artificial insemination has become an important economical means for breeding animals in agricultural industry, both as regards breeding of animals with specific preferred genetic characteristics and animal production in general.

However, there are some limitations in respect of obtaining pregnancies in the female animal by performing artificial insemination. For example, the shelf life and viability of the collected spermatozoa, both during storage, after thawing in case of cryopreserved spermatozoa, and after insemination, are essential for a successful breeding result. Whether suitable preservation techniques are available for the specific species of animals vary. For cattle, cryopreservation techniques are widely used. On the other hand, spermatozoa from other species such as swine are less tolerant to cryopreservation techniques, resulting in less flexibility as regards semen processing and storing possibilities.

Furthermore, to obtain spermatozoa with suitable fertilizing capacity, it is desired that the preservation method used also provides for maintenance of the fertilizing capacity after insemination. There has been a lot of focus and research for preservation methods aiming at providing storage methods and means which ensure that the spermatozoa maintain the fertilizing capacity for a longer time after collection and till the point of insemination.

If the shelf life is short as regards maintaining fertilizing capacity after insemination, it is more difficult to meet the preferred point of insemination with respect of ovulation. In case of short shelf life characteristic, good preservation techniques for spermatozoa that provide for longer shelf life and thus longer fertilizing capacity are vital. There is yet no preservation method available that provides sufficient shelf life and spermatozoa viability in a sufficient period after insemination to meet the breeders need for flexibility, especially when there is a long and time consuming transport distance between the location of the male and thus the place where semen collection is performed, and the female recipient.

Furthermore, a preservation method providing a more controlled and long-lasting availability of the spermatozoa would reduce the need for artificially provoked ovulation by hormone treatment. This would be beneficial both economically, according to consumer demands, and in respect of animal health.

Thus, there is a need for methods ensuring that the spermatozoa maintain the fertilizing capacity for a longer time after insemination, e.g. maintain the fertilizing capacity for a longer period when placed inside the female recipient.

At present, artificial insemination (AI) in cattle is widely performed using cryopreserved spermatozoa. Cryopreserved spermatozoa can be stored in liquid nitrogen for decades until used. However, when spermatozoa are thawed, AI has to be performed within a few hours. After insemination the cryopreserved spermatozoa have fertilizing potential for approximately 12-24 hours, and AI has to be performed within approximately 12-24 hours before ovulation. Thus, there is a need for preservation techniques for breeding of cattle providing spermatozoa which have sufficient shelf life characteristics and which preferably maintain fertilizing capacity for several days.

In some countries, liquid stored bull spermatozoa are used in order to reduce the number of sperm cells per AI dose. The spermatozoa have fertilizing capacity for approximately 24-36 hours before insemination. AI has to be performed within approximately 24 hours after spermatozoa collection. However, liquid preserved bull spermatozoa are encumbered with several drawbacks such as shortened/reduced shelf life and reduced scope of distribution.

In swine, cryopreserved spermatozoa are used only for special purposes like export, long distance shipment and for control of contagious diseases. AI in swine is usually performed with liquid preserved semen. The storage time for liquid preserved semen (spermatozoa) will depend on which extender is used. Spermatozoa diluted with short term extenders preserve the fertilizing capacity for approximately 2-3 days, while spermatozoa diluted with long term extenders may preserve the fertilizing capacity for up to 5-6 days. After insemination, fertilizing capacity of the spermatozoa lasts for approximately 12-24 hours. Most sows are inseminated twice during heat with approximately 24 hours interval. With a more flexible system providing longer storage time before insemination (e.g. one week) and/or prolonged storage and release of spermatozoa after insemination (e.g. more than 24 hours), the breeding industry would have more efficient production and distribution, and the breeders would have less need for accuracy in timing of insemination relative to ovulation.

In horse-breeding the breeder is mostly dependent on fresh spermatozoa due to lack of applicable preservation techniques for horse spermatozoa. This is a large problem in the horse-breeding and horse racing industry since the preferred stud for a specific brood mare most often is situated in a different country, requiring long transport time. In addition, due to the lack of suitable preservation methods for horse spermatozoa, AI of fresh horse spermatozoa must be performed within 24 hours after the spermatozoa collection. Horse breeding is thus attended with an undesired time pressure which often results in reduced sperm quality or reduced impregnation due to incorrect insemination in respect of ovulation.

Thus, there is a need for preservation methods that ensure both longer shelf life in respect of necessary delivery transport time and a longer shelf life after insemination. An applicable preservation method for horse semen would be of great economic and practical value, and would possibly revolutionize the horse breeding industry.

A spermatozoa preservation system that provides sufficient viability both during storage, before and after insemination would be beneficial for the breeding industry in general. A more flexible preservation system would render the breeding work for all species of animals easier and result in an increase in successful impregnation. A system where the breeder is less dependent on meeting the most preferable insemination point in time in respect of ovulation provides more flexibility.

In order to extend the fertilizing capacity of ejaculated spermatozoa, several preservation methods including cryopreservation and liquid preservation have been investigated.

Several studies of storage of spermatozoa within capsules have been published. These studies have used encapsulation methods that result in a particle where the spermatozoa are located within a liquid core surrounded by a semipermeable membrane.

Nebel et al. (1985), Microencapsulation of bovine spermatozoa. J. Anim. Sci. 1985 60(6):1631-39, describes a method for encapsulation of bovine spermatozoa in capsules made of alginate in combination with polylysin. This method is based on a previously published method from Lim and Sun (1980), Microencapsulated islets as bioartificial endocrine pancreas. Science 1980 210(4472):908-10, which was working with encapsulated insulin production from encapsulation of langerhans cells. Nebel et al. (1985), reported results both from storage at 37° C. and 335 inseminations, and results for encapsulated spermatozoa was compared to un-encapsulated control samples. No major differences between encapsulated and control samples was reported in this study. Other published studies has also demonstrated that spermatozoa can be encapsulated within capsules with similar methods, and maintain their functionality in vivo (Munkittrick et al. (1992) Accessory sperm numbers for cattle inseminated with protamine sulfate microcapsules. J. Dairy Sci., 75(3):725-31 (Bovine), Vishwanath et al. (1997) Selected times of insemination with microencapsulated bovine spermatozoa affect pregnancy rates of synchronized heifers. Theriogenology, 48: 369-76 (Bovine) and Maxwell et al. (1996). Survival and fertility of micro-encapsulated ram spermatozoa stored at 5° C. Reprod. Dom. Anim., 31:665-73(Sheep). Munkittrick et al. (1992) and Vishwanath et al. (1997) report however, that encapsulated spermatozoa are not as efficient as untreated spermatozoa when inseminated at the same time. This was explained with that encapsulated spermatozoa might need some time to be released from the capsules before fertilization can occur.

Conte et al. (1998), in EP 0922 451 B1 issued to Universitá di Pavia and Universitá Degli Studi Di Milano and Torre et al. (2002), Boar semen controlled delivery system: storage and in vitro spermatozoa release. J. Control. Release, 85:83-89, have developed an alternative method for encapsulation of boar spermatozoa. In this method, the spermatozoa are added to a solution containing calcium or barium, and this suspension is dripped into a solution containing alginate. A capsule of calcium or barium alginate is formed spontaneously round the drop as it hits the alginate solution. This method is claimed to be gentler to the cells compared to the method described by Nebel et al. (1985). Another advantage is that this method implies very little dilution of the spermatozoa solution, which is claimed to be beneficial for the viability of the cells.

Faustini et al. (2004), Boar spermatozoa encapsulated in barium alginate membranes: a microdensitometric evaluation of some enzymatic activities during storage at 18° C., Theriogenology, 61(1):173-184 reports a significant larger fraction of spermatozoa with intact acrosome, and less leakage of enzymes from spermatozoa stored encapsulated with this method compared to untreated spermatozoa stored under the same conditions.

In a recent paper Weber et al (2006), Design of high-throughput-compatible protocols for microencapsulation, cryopreservation and release of bovine spermatozoa. Journ. Biotechnol., 123:155-163, also describes a novel system for encapsulation of bovine spermatozoa. This system is designed for high-throughput manufacture of encapsulated spermatozoa using Ca-alginate or cellulose sulfate poly-diallyldimethyl ammonium chloride (pDADMAC) capsules.

Finally, Chou et al., U.S. Pat. No. 6,596,310 B1 (2003) discloses a method of artificial insemination by timed release of sperm from capsules or solid beads, wherein the sperm is maintained in a non-capacitated stage due to the use of an energy source that does not support capacitation.

SUMMARY OF THE INVENTION

The present invention is based on the surprising finding that embedding of spermatozoa within biopolymer matrixes, wherein the biopolymer matrix consists of alginate being rich in guluronic acid, results in spermatozoa with superior preservation characteristics in respect of shelf life, viability and fertilization. The biopolymer particles and the spermatozoa thereof may thus be used in artificial insemination of animals.

One non-limiting advantage of the present spermatozoa preservation biopolymer system is that it provides benefits by giving the spermatozoa fertilizing capacity for a longer period after insemination, and thus making the time of insemination relative to ovulation less critical.

The biopolymer particles according to the present invention may be used in breeding and in production of animals in the agriculture industry. The biopolymer particles are thus usable when the object is to provide animals with specifically desirable characteristics. The biopolymer particles are also usable when the object is to produce animals in general, e.g. for production of beef cattle.

According to the present invention, the biopolymer particles may be used directly and inseminated as such in the recipient animal if the biopolymer particle, such as alginate particles, will dissolve under physiological conditions within the recipient animal (i.e. within the uterus or cervix). The biopolymer particles according to the present invention thus provide for a controlled release of the spermatozoa. The spermatozoa may also be dissolved from the biopolymer particle prior to insemination of the spermatozoa.

As discussed above, the prior art mainly suggests encapsulation of spermatozoa in biopolymer capsules wherein the spermatozoa are contained in a liquid core of a biopolymer capsule. Only one reference (Chou et al., U.S. Pat. No. 6,596, 310 B1) mentions the possibility of embedding spermatozoa in a solid polymer matrix, although no examples of the solid beads described therein are shown.

The present inventors have instead found a different approach to immobilization of spermatozoa. According to the present invention, the spermatozoa are embedded within a solid gel-network made of alginate gels, wherein the alginate used is rich in guluronic acid. The present inventors have found that immobilization within a solid gel-network has several advantages compared to encapsulation within capsules and beads disclosed in the prior art.

Without being bound to a specific theory it is assumed that, by using the biopolymer particles and method according to the present invention, the embedding results in an immobilization, e.g. the natural movements of the spermatozoa are restricted due to constraints of the gel-network. A physical limitation of movement due to high concentrations of cells and presence of high viscosity polymers may be one of the factors that influence survival and maintenance of functionality of spermatozoa in the cauda epididymidis (Watson 1993). Spermatozoa are being stored for long periods of time (more than 1 week) in the cauda epididymidis (Watson 1993). The use of alginate being rich in guluronic acid render it possible to provide biopolymer particles comprising embedded spermatozoa which is useable in practice as a conservation system and which may be used in artificial insemination e.g. in breeding of animals.

Thus, according to one aspect, the invention provides biopolymer particle for preservation of spermatozoa, wherein the spermatozoa are embedded in a biopolymer gel network, and wherein the biopolymer particle embedding the spermatozoa comprises alginate being rich in guluronic acid.

According to another aspect of the present invention, the biopolymer embedding the spermatozoa comprises calcium alginate.

According to another aspect said biopolymer comprises alginate with low viscosity.

According to yet another aspect of the invention, the alginate concentration in the biopolymer particles of the invention is at least 0.1%.

According to yet another aspect of the invention, the alginate concentration in the biopolymer particles of the invention is between at least 0.1% and 6% alginate.

According to yet another aspect of the invention, the alginate concentration in the biopolymer particles of the invention is at least 1%.

Furthermore, according to one aspect of the invention, the spermatozoa concentration in the biopolymer particles are at least $0.1 \times 10^6$ spermatozoa/ml, such as e.g. at least $100 \times 10^6$ spermatozoa/ml, such as up to at least $2.5 \times 10^9$ spermatozoa/ml.

According to yet another aspect, the particles according to the present invention are stored in a solution, e.g. wherein the storage solution: biopolymer particle ration is at least between 1:1 and 1:100.

According to yet another aspect, the spermatozoa may be co-embedded with compounds or agents which are beneficial in light of the fertilizing capacity and/or animal health such as e.g. one or more of the compounds or agents selected from the non-limiting group consisting of extenders, cryoprotectants, antibiotics, antibodies, antioxidants, protein, and hormones According to another aspect of the invention, the spermatozoa are co-embedded with one or more antioxidants selected from the group consisting of pyruvate, 2,2,6,6-tetramethylpeperidin-1-oxyl, 4-hydroksy-2,2,6,6-tetra-metylpeperidin-1-oxyl, superoxide-dismutase, catalase, glutathionperoxydase, butylated hydroxytoluen, butylated hydroxyanisol.

According to one aspect, the biopolymer particles are coated. The coating may be selected from the non-limiting group consisting of polylysin, chitosan, cellulose sulphate, hydroxypropylmethylcellulose, and polydiallyldimethyl ammonium chloride.

The biopolymer particles according to the present invention comprises spermatozoa collected from an animal selected form the non-limiting group consisting of swine, cattle, horses, sheep, goats, rabbits, poultry, pets like pedigree dogs, aquatic animals and endangered animal species, preferably swine, cattle, fur animals and horses. The biopolymer particle of the present invention may thus be used in obtaining pregnancies in an appurtenant female animal by commonly artificial fertilization methods like AI, IVF and ICSI.

According to one aspect of the invention, the spermatozoa used to form said particle are contained in seminal fluid.

Optionally, the biopolymer particle may be further treated by dehydration, cryopreservation or freeze-drying The invention also provides a process for the preparation of the particles according to the invention, wherein a mixture of alginate being rich in guluronic acid and spermatozoa is added drop by drop to a gelling solution. The gelling solution comprises according to one aspect of the invention one or more of the following ions selected from the non-limiting group consisting of calcium, sodium, barium and magnesium, preferably, calcium and sodium ions.

Furthermore, the biopolymer particles may optionally be formed directly in a semen container.

According to one aspect of the process of the invention, the particles are further treated by dehydration, cryopreservation or freeze-drying.

The present invention also provides the use of the biopolymer particles according to the present invention in breeding of animals, such as swine, cattle, horses, sheep, goats, rabbits, poultry, pets like pedigree dogs, fur animals, aquatic animals and endangered animal species. According to one aspect of the invention, the biopolymer particles are used in breeding of swine, cattle or horses. According to one aspect, the particles are inseminated directly. According to yet another aspect, the particles are dissolved before insemination. According to yet another aspect the particles of the invention are used together with free, immobilized spermatozoa.

Finally, the present invention provides a process for fertilization of an animal, wherein spermatozoa preserved in particles according to the present invention is introduced in a recipient female animal.

DETAILED DESCRIPTION OF THE INVENTION

Figure 1:
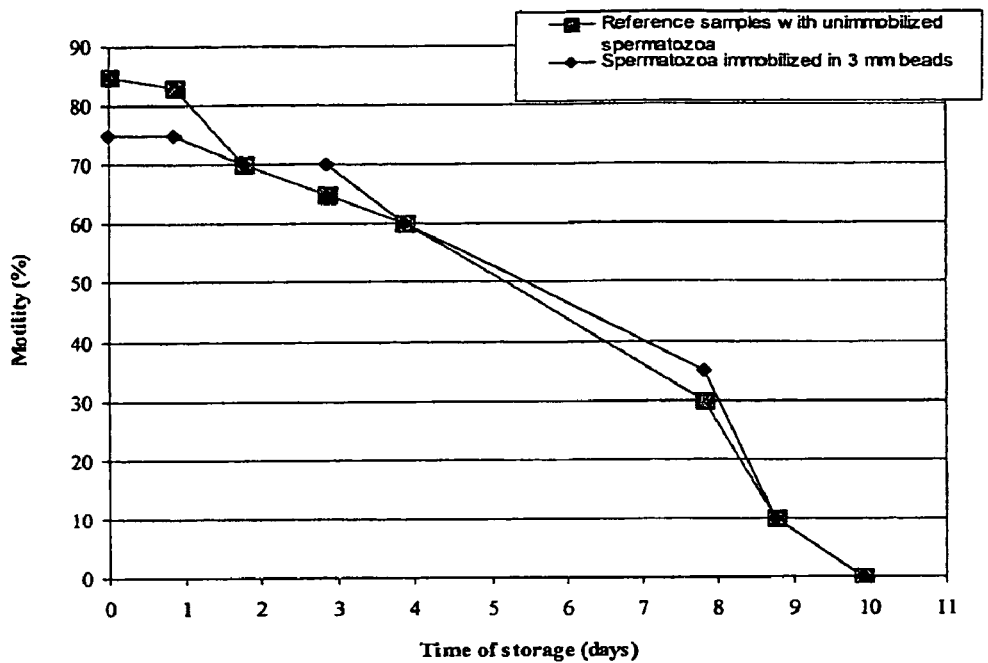
FIG. 1 shows in-vitro storage of bovine (Pane A) and boar (Pane B) spermatozoa at ambient temperatures (bovine 20° C., boar 18° C.). Values of motility are given as functions of time of storage in reference samples and in samples with immobilized spermatozoa.
Figure 1:
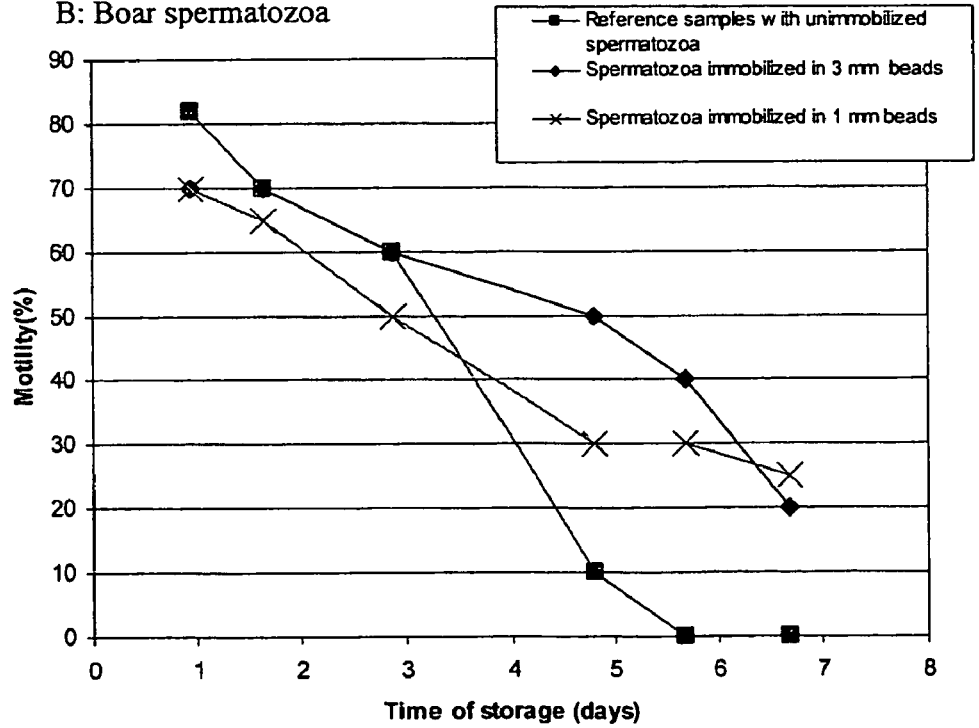

As previously described, the main focus of research has previously been directed towards encapsulation of spermatozoa in order to facilitate in-vitro fertilization and artificial insemination. The present inventors have taken a fundamentally different approach to immobilization of spermatozoa, wherein the spermatozoa is embedded within a gel or biopolymer network inside a solid gel-particle and wherein the biopolymer network consists of alginate being rich in guluronic acid. This approach is fundamentally different from the encapsulation of spermatozoa previously described in the prior art, wherein spermatozoa is contained within a capsule with a liquid core wherein the spermatozoa may move around as in their natural environment. The biopolymer particles embedding the spermatozoa according to the present invention are not dependent on the use of solutions ensuring that the spermatozoa is maintained in a non-capacitated state.

The term "embed" or "embedding" as used herein should be understood as immobilizing spermatozoa resulting in that the spermatozoa are prevented from having their natural possibility of movement. The degree of immobilization will vary dependent on the characteristics of the biopolymer particle, such as e.g. mechanical strength, and type of polymer used. However, it is to be understood that the spermatozoa embedded in the biopolymer particles according to the present invention are prevented from having their natural possibility of movement that the spermatozoa otherwise would have if they were stored in liquid, such as in a liquid core of a capsule.

The term "biopolymer particle" as used herein means a particle, which when comprising spermatozoa, provides for a reduced possibility of movement. The biopolymer particles according to the present invention are comprised of a material forming a network consisting of an alginate gel being rich in guluronic acid. The function of the biopolymer particle in respect of preserving spermatozoa is independent of the three-dimensional shape of the biopolymer particle according to the present invention. Thus, the biopolymer particles according to the present invention may have different shapes such as e.g. a spherical or cylindrical shape.

Alginate is a polymer which consists of the guluronic acid (G) and mannuronic acid (M). Alginate is a common constituent of cell wall in all species of the brown seaweeds (*Phaeophyceae*) and is commonly extracted by alkaline solution. The ratios of mannuronic acid to guluronic acid (M/G) in alginate vary widely dependent on the specific alginophytes (alginate producing seaweed) and throughout the various seasons.

Alginate is also synthesized by Pseudomonas and Azotobacter bacteria (Svanem et al., (2001), The Journal of Biological Chemistry, Vol 276:34, 31542-31550, Jain et al., (2003), Molecular Microbiology, 47(4), 1123-1133, Scott and Quatrano (1982), Applied and Environmental Microbiology, 44:3, 754-756.

Alginates are widely used e.g. in food industry as e.g. stabilizers and for viscosity control, in pharmaceutical and cosmetic industry as e.g. disintegrant. For the various purposes, both alginates being rich in guluronic acid or mannuronic acid, respectively, are available (Mancini et al., (1999), Journal of Food Engineering 39, 369-378) and various methods for producing alginates being rich in guluronic acid are known, cf. WO 8603781, U.S. Pat. No. 4,990,601, U.S. Pat. No. 5,639,467).

The term "alginate being rich in guluronic acid" or "G-rich alginate" as used herein means alginate comprising higher amounts of guluronic acid than mannuronic acid in the polymer chains comprising the polysaccharide. Examples of the understanding of the term "G-rich", as commonly used by persons skilled in the art, are evident from the prior art set out in the two preceding paragraphs.

Alginate gels are formed due to interactions between divalent ions such as $Ca^{2+}$ and blocks structures of the guluronic acid in the alginate polymer chain. Therefore, the formation of alginate gels can be done at very mild conditions, and is suitable for immobilization of a cell. Alginate gels have thus been commonly used for immobilization of various types of cells. However, immobilization in alginate is most commonly used as a starting point for later formation of various types of capsules with a liquid core.

When herein after referring to alginate, alginate gel, alginate network or biopolymer particle according to the present invention, it is to be understood that said alginate, alginate gel, alginate particle or biopolymer network or particle according to the present invention is rich in guluronic acid.

Non-limiting examples of suitable alginate types are FMC LF 10/40, FMC LF 10/60 and FMC LF 20/60 available from FMC Biopolymer AS, Drammen, Norway or A2033 from Sigma, Oslo, Norway.

The term "shelf life" as used herein means the time that the spermatozoa maintain the fertilizing capacity, both in respect of in vitro storage before insemination and in vivo after insemination in the recipient animal. The specific shelf life of spermatozoa of different origin may vary. Nevertheless, the present preservation system, wherein spermatozoa is embedded in biopolymer particles according to the present invention provides for a longer shelf life after insemination compared with spermatozoa which are inseminated after conventional storage methods after semen collection. According to one example of the invention, swine spermatozoa maintain excellent fertilizing capacity for more than 12 hours after insemination, more preferably more than 24 hours after insemination. According to yet another example of the invention, bull spermatozoa maintains excellent fertilizing capacity for more than 12 hours after insemination, more preferably more than 24 hours after insemination The term "breeding" as used herein means any method used to achieve pregnancy in a female animal. A non-limited list of such methods includes IVF, artificial insemination and ICSI. Furthermore, breeding encompass both breeding in respect of providing animals having specifically desirable characteristics and in respect of commercial production.

The term "spermatozoa" as used herein includes spermatozoa as such and also spermatozoa contained in seminal fluid. i.e., semen may be used directly when forming the biopolymers according to the present invention. However, also spermatozoa isolated from the seminal fluid, optionally contained in other suitable storage solutions, may also be used to form the biopolymer particles according to the present invention.

The term "semen container" as used herein includes all types of packaging suitable for the keeping and storage of spermatozoa.

The previous encapsulation methods disclosed in the prior art and as discussed above is laborious and the immobilization procedures normally contain several steps. However, the preparation of biopolymer particles according to the present invention may be prepared in a one step procedure. More exactly, calcium alginate particles containing spermatozoa are easily formed with minimal physiological and chemical stress to the immobilized cells. Alginate particles can be made in various sizes and shapes, and with varying alginate types, alginate concentrations and concentrations of immobilized spermatozoa.

For the purpose of embedding spermatozoa according to the present invention, the use of alginate as the biopolymer material is particularly suitable due to the fact that i) one may form gels during mild conditions, ii) alginate is non-toxic both in respect of the spermatozoa and the recipient animal, and iii) alginate dissolves under physiological conditions and thus is able to release the spermatozoa within the uterus or cervix.

According to one aspect of the present invention, the alginate particles are prepared by adding a solution comprising alginate and spermatozoa drop by drop into a gelling solution resulting in the formation of alginate beads with the spermatozoa embedded therein.

The preparation of alginate beads are known to the skilled person in the art, e.g. as disclosed in Smidsrød, O. and Skjåk-Bræk, G. (1990) Alginate as immobilization matrix for cells. *Trends in Biotechnology* 8, 71-78 and U.S. Pat. No. 6,497, 902.

Various gel solutions may be applied to form biopolymer particles such as alginate beads. The various solutions that are suitable for forming various biopolymer particles are well within the knowledge of the skilled person. According to the present invention, bivalent ions (also called gelling ions herein) such as calcium and barium may be used to form the alginate particles, e.g. to achieve gelling of the alginate. Alginate forms gels in the presence of many bivalent ions and multivalent ions. The use of calcium ions results in fast gelling and relatively strong particles. On the other side, the use of barium ions results in even stronger particles which are more stable under physiological conditions. It is to be understood that the type and amount gelling ion to be used to form biopolymer particles according to the present invention may vary according to inter alia the desired strength of the gel formed, the type of and concentration of the alginate used, the guluronic acid content and the G-block length of the alginate, the type and source of spermatozoa used, type of additional agents to be incorporated in the particles (such as antibiotics, extenders, antioxidants etc), and that such modifications are within the scope of the present invention. Based on prior art and the guidance of the present specification, the skilled person would identify and determine, without undue burden, various compounds that may be co-embedded with the spermatozoa in the biopolymer particles according to the present invention.

According to one aspect of the present invention, calcium ions and sodium ions are used to form biopolymer particles. Thus, by varying the alginate concentration and degree of cross binding, one may obtain particles with various spermatozoa release characteristics and which e.g. is adapted to specific species of animals or specific ovulation conditions in various animals.

In addition, the concentration of the alginate influences on the mechanical characteristics of the biopolymer particles, and thus also the dissolution characteristics of the particles. The alginate concentration may thus vary dependent on the dissolution characteristics needed in each case dependent on e.g. the recipient animal. The skilled person will, based on his general knowledge and based on the guidance herein and without undue burden determine the various applicable concentrations of G-rich alginate to use when preparing biopolymer particles according to the present invention. According to one aspect of the invention, the alginate concentration in the biopolymer particles according to the present invention is between at least 0.1 and 6%.

The concentration of spermatozoa embedded in the biopolymer particles according to the present invention may vary dependent on e.g. type/source of spermatozoa, breed, recipient animal, insemination technique or system, fertilizing techniques or system, the presence of other agents included in the particles (antibiotics, antioxidants, extenders, proteins, etc). In principle there is no lower limit of the spermatozoa concentration, and the concentration may vary dependent of e.g. the fertilization method, the origin of the spermatozoa, the recipient animal, the dissolution characteristics of the biopolymer particles etc. With the guidance of the present specification and general knowledge, the skilled person would without undue burden of experimentation determine the suitable spermatozoa concentration to be used in each case based on the desired fertilization method, origin of spermatozoa, recipient animal etc. It is to be acknowledged that lower amounts of spermatozoa may be used when ICSI is used as the desired fertilization method compared to e.g. artificial insemination.

According to one aspect of the invention, the spermatozoa concentration is thus at least $0.1 \times 10^6$ spermatozoa/ml.

Figure 4:
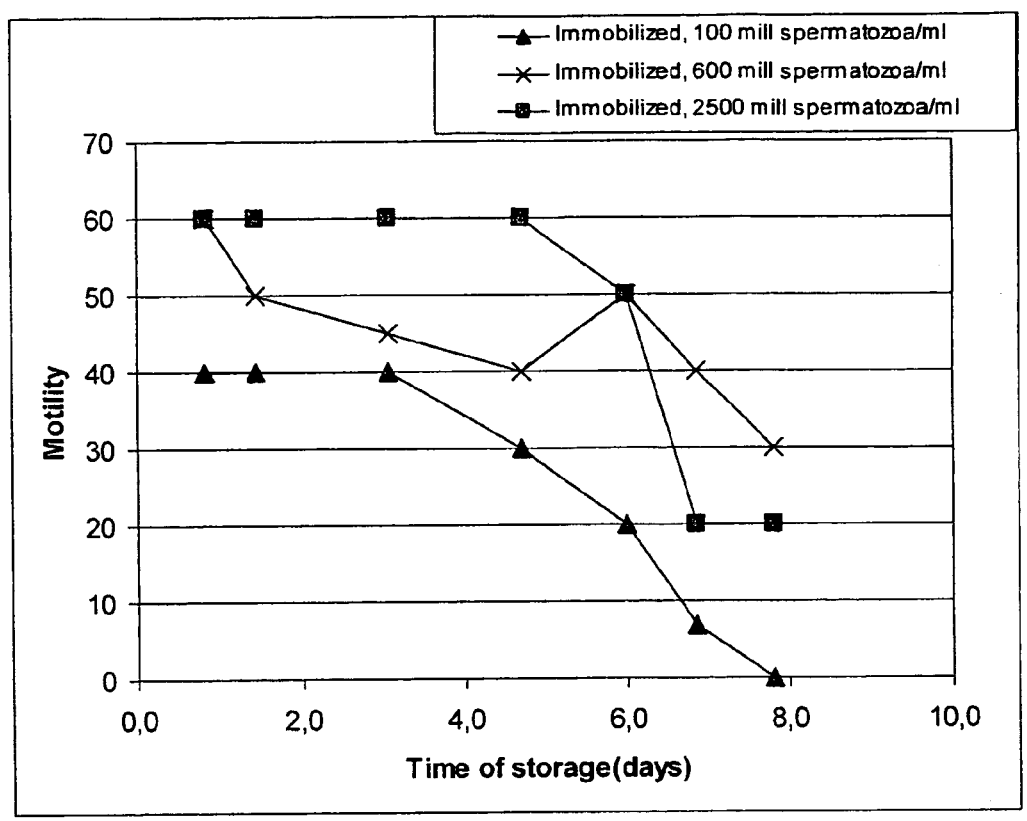
FIG. 4: In-vitro storage of boar spermatozoa at ambient temperatures (18° C.). Values of motility are given as functions of time of storage in samples with immobilized spermatozoa. Beads with different concentrations of immobilized spermatozoa are used in the storage experiments, as indicated in the series name. The spermatozoa are immobilized in beads with a diameter of 3 mm.

The findings of the present invention show that for some animals, the survival of the spermatozoa is highly increased with increasing concentration of spermatozoa. Thus, according to one example of the present invention, at least $2.5 \times 10^9$ swine spermatozoa/ml is embedded in the biopolymer particle (cf. FIG. 4). However, $100 \times 10^6$ swine spermatozoa/ml also results in pregnancies in the female animal. For bull spermatozoa, the same concentration range as for swine spermatozoa are applicable.

The concentration of the spermatozoa in the biopolymer particles may furthermore be modified by changing the amount of spermatozoa relative to the amount of alginate before gelling, or by concentration or diluting the spermatozoa solution prior to mixing the alginate solution and the solution comprising spermatozoa. However, since the modification of the amount of spermatozoa finally results in a modification of alginate concentration in the particles obtained, the alginate concentration in the starting alginate solution must be adjusted if the concentration of the alginate in the biopolymer particles is to be maintained. Due to the high viscosity of alginate in solution, it might be practically difficult to use alginate solution with more than 4-6% alginate. Thus, according to one aspect of the invention, the biopolymer particles are composed of alginate with low viscosity.

In addition, the spermatozoa embedded in the biopolymer particles according to the present invention are somewhat isolated from the surrounding environment, and are not released until the calcium alginate gel network is dissolved. Furthermore, the calcium alginate gel network dissolves slowly under physiological conditions, which causes a slow release of spermatozoa from the immobilization matrix. Due to this effect, spermatozoa with fertilizing capacity may be present for longer periods of time. The rates of dissolution can be controlled using different types of coating on the immobilization matrix. Various useful coatings are known, including but not limited to polylysin, chitosan, cellulose sulphate, hydroxypropylmethylcellulose or polydiallyldimethylammonium chloride.

To further improve spermatozoa quality, the spermatozoa may be co-embedded in with various solutions of importance to spermatozoa survival and vitality. According to one embodiment of the invention, an extender is included in the biopolymer particle of the present invention.

Spermatozoa extenders are commonly used for several purposes:
- to increase the volume
- to standardize the sperm number in the AI dose
- to perform buffer capacity
- to provide physiological environment in respect to osmolarity
- to support nutrition to the sperm cells
- to control microbiological contamination (antibiotics), or in case of cryopreservation:
- to protect sperm cells from cryo and thawing injuries.

It is well within the knowledge of the skilled person to select an appropriate extender that may be used in biopolymer particles according to the present invention, based on e.g. type of spermatozoa (origin), species, preservation method, storage temperature, insemination method, zoosanitary requirements, and international legislation. Milk extenders and TRIS are only a few non-limiting examples of extenders among a huge number of applicable, commercial available spermatozoa extenders. Another useful extender are the extender reported in Aalbers, J G, Rademaker, J H M, Grooten, H J G and Johnson, L A, 1983: Fecundity of boar semen stored in BTS, Kiev, Zorlesco and Modena extenders under field conditions. J. Anim. Sci. 75 (Suppl. 1), 314-315 and Aalbers, J G, Johnson, L A, Rademaker, J H M and Grooten H J G, 1984: Use of boar spermatozoa for AI: fertility and morphology of semen diluted in BTS and used for insemination within 24 hrs or 25 to 48 hrs after collection. Proc. 10th Int Congr. Anim. Reprod and Artif. Insemin. Urbana Ill., Vol II, No 180, pp 1-3, commonly known as the BTS. BTS is commercial available from Minitüb i Tyskland. (Minitüb Abfüll-und Labortechnik GmbH & Co. K G, Hauptstrasse 41, DE-84184 Tiefenbach, Germany.

Yet another useful extender is the Tri X-Cell™ extender commercial available from IMV (Instrument de Medecine Veterinaire, 10, rue Georges Clemenceau, B. P. 81, FR-61302 L'AIGLE Cedex, France).

The various extenders differ in composition, pH, buffer capacity, osmolarity and antibiotics. Many are published while others are commercial secrets. The simplest extenders are composed only of different sugar solutions, as e.g. lactose and glucose. Based on general knowledge of the skilled person within the field of sperm preservation, it will be understood that various extenders may be used according to the present invention. The type of extenders used according to the present invention may vary dependent on the origin of the sperm, type of polymer used, preservation method, storage temperature, etc. It is well within the knowledge of the skilled persons to determine and choose the type and suitable amount of extender used without departing from the scope of the invention disclosed in the specification and the enclosed claims.

The biopolymer particles according to the present invention may be formed in various sizes according to methods known in the prior art. Which size is suitable is dependent on various factors such as spermatozoa source, type and size of fertilizing device used, size and shape of semen container used etc. The biopolymer particles according to the present invention may be formed with a diameter suitable for all prior art insemination techniques, to enable easy manipulation, handling, transportation and preservation.

According to yet another aspect of the invention, the biopolymer particles are formed within a container, such as e.g. an insemination straw, resulting in particles perfectly adjusted to the size of the container. Thus, in a case of forming the biopolymer particles within a container, no further storage solution may be necessary.

According to one aspect of the invention, the biopolymer particles comprise spermatozoa collected from cattle. According to yet another aspect of the invention, the present biopolymer particles comprise spermatozoa collected from swine.

Although the present invention is illustrated by alginate particles comprising spermatozoa collected from cattle and swine, respectively, the biopolymer particles may also embed spermatozoa from other species of animals. Without limitation, the biopolymer particles may also embed spermatozoa collected from e.g. horses, sheep, goats, rabbits, poultry, pets like pedigree dogs, aquatic animals and various endangered species.

In addition there are no indications what so ever that the present biopolymer particles might not be useful in the preservation of human spermatozoa and thus useful in the treatment of childlessness. Thus, it is to be understood that the term "animal" as used herein also covers human beings.

In addition, spermatozoa preservation techniques are also widely demanded in the aquaculture industry. Thus, also spermatozoa which originate from aquatic animals might be embedded in the biopolymer particles according to the present invention and are thus also covered by the term "animal" as used herein.

Immobilization of spermatozoa within a biopolymer gel network can also be used to create a microenvironment which is beneficial for storage of spermatozoa, even within the female reproductive organs. This can be done with further co-embedding solutions which are beneficial in respect of the spermatozoa, the degree of fertilization, animal health etc. For example, non-limited examples of substances which enhance viability during storage are antioxidants or proteins, hormones etc. The spermatozoa may also be co-embedded with other agents or compounds which are beneficial in light of the fertilizing capacity or animal health. Such agents or compounds may be e.g. antibiotics, such as e.g. streptomycin, neomycin, gentamycin, penicillin, lincomycin, spectinomycin, amoxicillin, tylosin, etc., which may be used to control or prevent venereal diseases, cryoprotectants, antibodies, hormones, or compounds increasing the reproductive efficiency, e.g. such as the compounds known from U.S. Pat. No. 5,972, 592.

Thus, according to still another aspect of the invention, the biopolymer particles comprise in addition to spermatozoa, compounds which are beneficial in respect of fertilizing capacity or animal health, such as e.g. antioxidants, antibiotics, antibodies, hormones or reproductive efficiency increasing agents or combinations thereof. According to one preferred embodiment of the present invention, the biopolymer particles comprise antioxidants, e.g. such as pyruvate.

The biopolymer particles according to the present invention may optionally be stored in well known spermatozoa storage solutions, such as e.g. milk extenders, PBS (phosphate buffered saline), BTS, Tri X-Cell™, EDTA-extenders, Kiev-extenders, Modena, MR-A, Androhep, Acromax, Triladyl®, Biladyl®, Bioxcell, Biociphos plus etc., with or without antioxidants such as e.g. pyruvat, 2,2,6,6-tetramethylpeperidin-1-oxyl (commonly abbreviated to Tempo), 4-hydroksy-2,2,6,6-tetra-methyl-peperidin-1-oxyl (commonly abbreviated to Tempol), superoxide-dismutase, catalase, glutathionperoxydase, butylated hydroxytoluen (commonly abbreviated to BHT), butylated hydroxyanisol (commonly abbreviated to BHA). The choice of storage solution is not critical as long as the storage solution does not comprise compounds which may negatively affect the characteristics of the biopolymer particles. For example, in case of alginate particles, the storage solution should not comprise too much chelators resulting in the withdrawal of the bivalent ions and thus dissolution of the gel.

During storage, the proportion of biopolymer particles relative to the storage solution may vary dependent on the type and concentration of G-rich alginate, source of spermatozoa, the fertilization method used etc. According to examples of the present invention, the storage solution: biopolymer particle ratio is at least 1:1, such as e.g. at least 1:2, at least 1:3, at least 1:4, at least 1:5, at least 1:6, at least 1:7, at least 1:8, at least 1:9 or at least 1:10. A storage solution: biopolymer particle ratio up to at least 1:100 may be used according to the present invention.

Furthermore, the biopolymer particles according to the present invention may optionally be stored both under ambient temperature, e.g. at 18° C. or 20° C., physiological temperature (37° C.), or at chilled conditions, e.g. at 5° C. In addition, the biopolymer particles may be further treated by dehydration, cryopreservation or freeze-drying. The biopolymer particles are then in case of cryopreservation thawed before insemination.

Spermatozoa which usually are liquid preserved may be stored for a longer period of time when embedded in a biopolymer particle according to the present invention. According to another embodiment of the invention, the biopolymer particles are used directly to inseminate a recipient animal. Optionally, the biopolymer particles may be dissolved to release the spermatozoa before insemination. However, the biopolymer particles may also according to still another embodiment be used together and in combination with free spermatozoa.

While this invention has been described in connection with specific embodiments thereof, it will be understood that it is capable of further modifications. This application is intended to cover any variations, uses or adoptions of the invention following, in general, the principles of the invention and including such departures from the present disclosure as come within the known and customary practice within the art to which the invention pertains and as may be applied to the essential features disclosed above and in accordance with the scope of the enclosed claims.

The foregoing description of the various aspect of the present invention reveals the general nature of the invention and the skilled person will by applying the general knowledge within the area of artificial insemination and breeding technology (including the contents of the references cited herein), readily modify and/or adapt the present biopolymer particles and the preparation and use thereof for various applications, without undue experimentation, without departing from the general concept of the present invention and the scope of the enclosed claims. Such adaptations or modifications are thus intended to be within the meaning of a range of equivalents of the disclosed embodiments, based on the teaching and guidance presented herein. It is to be understood that the terminology used herein is for the purpose of description and not of limitation. Thus, the terminology of the present specification is to be interpreted by the skilled person in light of the teachings and guidance presented herein, in combination with the knowledge of the skilled person.

The following non-limiting examples further illustrate the present invention.

EXAMPLES

Example 1

Immobilizing Spermatozoa in Alginate

Materials at Methods
Materials
The following chemicals were used: $CaCl_2.H_2O$, $K_2HPO_4$, $NaH_2PO_4$, NaCl, and sodium citrate from Riedel de Haën (Seelze, Germany); glucose monohydrate from Norsk Medisinaldepot (Oslo, Norway); sodium alginate (PROTANAL LF 10/60) supplied from FMC Biopolymer A/S (Drammen, Norway);

Source of Spermatozoa
Bovine spermatozoa were collected at the Geno facility at Hallsteingård in Trondheim, Norway. The boar spermatozoa were collected at the Norsvin facility at Hamar, Norway. Bovine spermatozoa were diluted 1+2 in milk extender shortly after ejaculation. Boar spermatozoa were diluted 1+4 in TRI X-CELL™ (IMV Technologies, L'Aigle Cedex, France). This dilution nor the choice of dilution buffers is not critical for the immobilization procedure or the long term survival of the spermatozoa after immobilization but is merely done in order to facilitate storage until the spermatozoa could be further processed.

Buffer Solutions
The following culture media were used. Modified IVT: 3 g $l^{-1}$ glucose, 20 g $l^{-1}$ sodium citrate, 2.1 g $l^{-1}$ $NaHCO_3$, 1.16 g $l^{-1}$ NaCl, 3 g $l^{-1}$ EDTA, pH 7.35. BTS (with 3 mM Ca): 37 g $l^{-1}$ glucose, 0.44 g $l^{-1}$ $CaCl_2$, 4.5 g $l^{-1}$ sodium citrate, 1.25 g $l^{-1}$ $NaHCO_3$, 1.25 g $l^{-1}$ EDTA, 0.74 g $l^{-1}$ KCl, 1 g $l^{-1}$ Neomycin, pH 7.2. Bead gelling solution: 7.3 g $l^{-1}$ $CaCl_2$, 5.96 g $l^{-1}$ NaCl. Milk extender: 110 g $l^{-1}$ Molico skimmed milk, 120 ml $l^{-1}$ egg yolk, 6.25 g $l^{-1}$ Strepomycin, 1.5 mill I.E $l^{-1}$ penicillin Cell Immobilization
Spermatozoa cells were harvested at the Geno or Norsvin facilities and diluted as described above. Before immobilization the spermatozoa were concentrated by centrifugation (800 g, 20 min, 20° C.). The amount of supernatant to be removed in each batch depends on the desired concentration of spermatozoa in the finished beads. After removal of excess supernatant, the cell pellet is gently resuspended by mild shaking. The cell suspension is then gently mixed with sterile 6% (w/v) sodium alginate solution. The alginate solution is added in volumetric ratio of 2 parts of cell suspension to 1 part of alginate solution (A large number of different combinations of alginate concentration, volumetric ratios of alginate solution and cell suspension have been investigated. Typical values and procedures are given here).

The mixture of alginate and cells is added drop-wise into bead gelling solution (see above). In order to produce beads with a diameter of 3 mm the solution is added through syringe tips with an inner diameter of 0.5 mm. In order to produce beads with smaller diameters (down to less than 1 mm in diameter) a system based on using airflow in order to limit the droplet size that forms on the needles is used. Sodium chloride is used in the gelling solution in order to ensure a homogeneous polysaccharide concentration throughout the beads (Smidsrød, O. and Skjåk-Braek, G. (1990) Alginate as immobilization matrix for cells. *Trends in Biotechnology* 8, 71-78). In order to limit the amount of $Ca^{2+}$ in the beads, the beads are stirred no more than 8 min in the bead gelling solution. The entire immobilization procedure is performed at ambient temperatures.

Storage of Immobilized Spermatozoa In Vitro at Ambient Temperature

One objective of the immobilization procedure is to lengthen the time the spermatozoa can be stored before insemination. Experiments were therefore conducted in which the spermatozoa are stored in vitro at ambient temperature in buffer solutions. Reference samples with un-immobilized spermatozoa from the same ejaculate are included in all experiments. The quality of the spermatozoa is evaluated by measurements of motility at different time points during the storage period. At each time point, samples are analyzed and the motility of the immobilized spermatozoa and the motility of control samples are recorded. A number of combinations of storage volumes and cell densities have been investigated in order to optimize the experimental system (Data not shown). The experimental conditions described below are typical, and were used in the experiments reported below.

In experiments with bovine spermatozoa, approximately 2 ml beads with immobilized spermatozoa were transferred to 13 ml centrifuge tubes and added milk extender solution at volumetric ratio of 1+2. Control samples with freely suspended spermatozoa are made by doing a total dilution of 1+15 in 13 ml centrifuge tubes (A volume of approximately 6 ml is used in all tubes). This dilution has in previous experiments been shown to be near optimal for sustaining motility during storage in the reference samples (Data not shown).

In experiments with boar spermatozoa, the spermatozoa were stored at 18° C. in BTS (with 3 mM Ca). In the experiments reported below, the control samples were diluted 1+10 in all experiments, giving a total volume of 20 in 50 ml centrifuge tubes (This dilution has previously been shown to be optimal for sustaining motility during storages). Beads containing immobilized spermatozoa were transferred to 50 ml centrifuge tubes and added BTS (with 3 mM CaCl2) in a ratio of 1+3. Beads containing immobilized spermatozoa were rinsed with the storage solution before transfer to storage solution.

Storage of Immobilized Spermatozoa at 37° C.

In order to assess the survival of the spermatozoa at physiological temperatures, the motility of the spermatozoa were recorded during storage of spermatozoa at 37° C. Bovine spermatozoa were transferred to a buffer solution prior to the storage experiments at 37° C. As described above, reference samples from the same ejaculate were included in each experiment. The tests were performed in 13 ml centrifuge tubes with a total volume 8 ml in each tube. Reference samples were diluted 1+4 in the storage solution. For immobilized spermatozoa, 3 ml of beads containing spermatozoa were added to 6 ml of buffer solution and stored in a 13 ml centrifuge tube. Boar spermatozoa were treated in a similar manner, except that a normal BTS (with 3 mM Ca) was used.

Assessment of Motility

The motility of the spermatozoa was assessed through a microscopic evaluation. Samples (typically 1 ml) were withdrawn from the storage containers and transferred to 1.5 ml Eppendorf tubes. The tubes were allowed to preheat for minimum 15 minutes in a heat-block at 37° C. prior to assessment. At the time of measurement, 2.5 µl of sample was added to a preheated microscope slide and immediately inspected using a light microscope. The number of motile spermatozoa in each sample was estimated to the nearest 5% interval. If practically possible, the operator was kept unaware of the sample identity during the assessment.

Immobilized spermatozoa must be released from the beads before evaluation of motility. In order to dissolve the alginate beads 1 part of beads was added to 3 parts of IVT solution in a 13 ml centrifuge tube. The tubes were then placed in a tube-tumbler and allowed to mix for approx. 30 min prior to the assessment.

Results and Discussion

Survival of Immobilized Spermatozoa

Data from experiments with storage of spermatozoa in reference samples (with un-immobilized spermatozoa) and samples with immobilized spermatozoa are shown in FIG. 1 for both bovine and boar spermatozoa. For boar spermatozoa data from 2 different bead sizes are shown. The reason for this is that the bead size must be below 1 mm in order to use beads for intrauterine insemination with the existing available equipment.

As can be seen from the data presented in FIG. 1, the immobilized spermatozoa seem to have a somewhat lower motility than the spermatozoa in the reference samples shortly after immobilization. This difference in motility can be caused both by the immobilization procedure or the dissolving procedure, as the beads containing immobilized spermatozoa must be dissolved prior to motility assessment. There is, however, no need to dissolve the beads prior to insemination, as the beads will dissolve slowly at physiological conditions (data not shown).

The difference in motility between reference samples and immobilized spermatozoa is reduced during the storage period as the motility in the reference samples seem to drop faster than in the immobilized samples, especially for boar spermatozoa. For immobilized boar spermatozoa, a motility of approximately 50% was recorded after 5 days of storage in beads with 3 mm diameter in this particular experiment. At this time, a motility of 10% was recorded in the reference samples. These results indicate that immobilization influences cells or the local environment of the cells in a manner that is beneficial for their ability to tolerate in-vitro storage at 18° C.

For bovine spermatozoa there is no significant difference in motility between the reference samples and the immobilized spermatozoa in the later period of the experiment shown.

Further optimization of the storage conditions and immobilization procedure may, however, improve the times of storage of immobilized bovine spermatozoa. Measurements of consumption of glucose and production of lactate of immobilized bovine spermatozoa and un-immobilized spermatozoa in reference samples indicate that spermatozoa stored within a calcium alginate gel network has a reduced rate of metabolism (c.f. Example 2).

In order to evaluate whether immobilized spermatozoa will survive physiological conditions, i.e. conditions where the activity of the spermatozoa ought to be at maximum, storage experiments were conducted at a temperature of 37° C. Data from experiments with in-vitro storage of bovine and boar spermatozoa during storage at 37° C. are shown in FIG. 2.

As seen in the experiments with in-vitro storage at ambient temperatures, there is a difference in motility between the reference samples and the samples with alginate immobilized spermatozoa after preparation of the samples. However, for both bovine and boar spermatozoa the motility drops fairly rapidly in the reference samples with un-immobilized spermatozoa during storage at 37° C. In the samples with immobilized spermatozoa, the motility drops significantly slower. After 15 hours of in-vitro storage at 37° C., the motilities of boar spermatozoa in both bead sizes are still above 50%. In fact, the motility is still approximately 30% after 60 hours of storage at 37° C. in beads with 3 mm diameter.

For bovine spermatozoa the motility seems to drop faster than for boar spermatozoa in this experimental system. However, as with boar spermatozoa there is a significant difference between in rates of motility drop during storage in this experiment for bovine spermatozoa. After 24 hours of storage, the immobilized bovine spermatozoa still has a motility of 45%, while there is no recorded motility in the reference samples.

Figure 2:
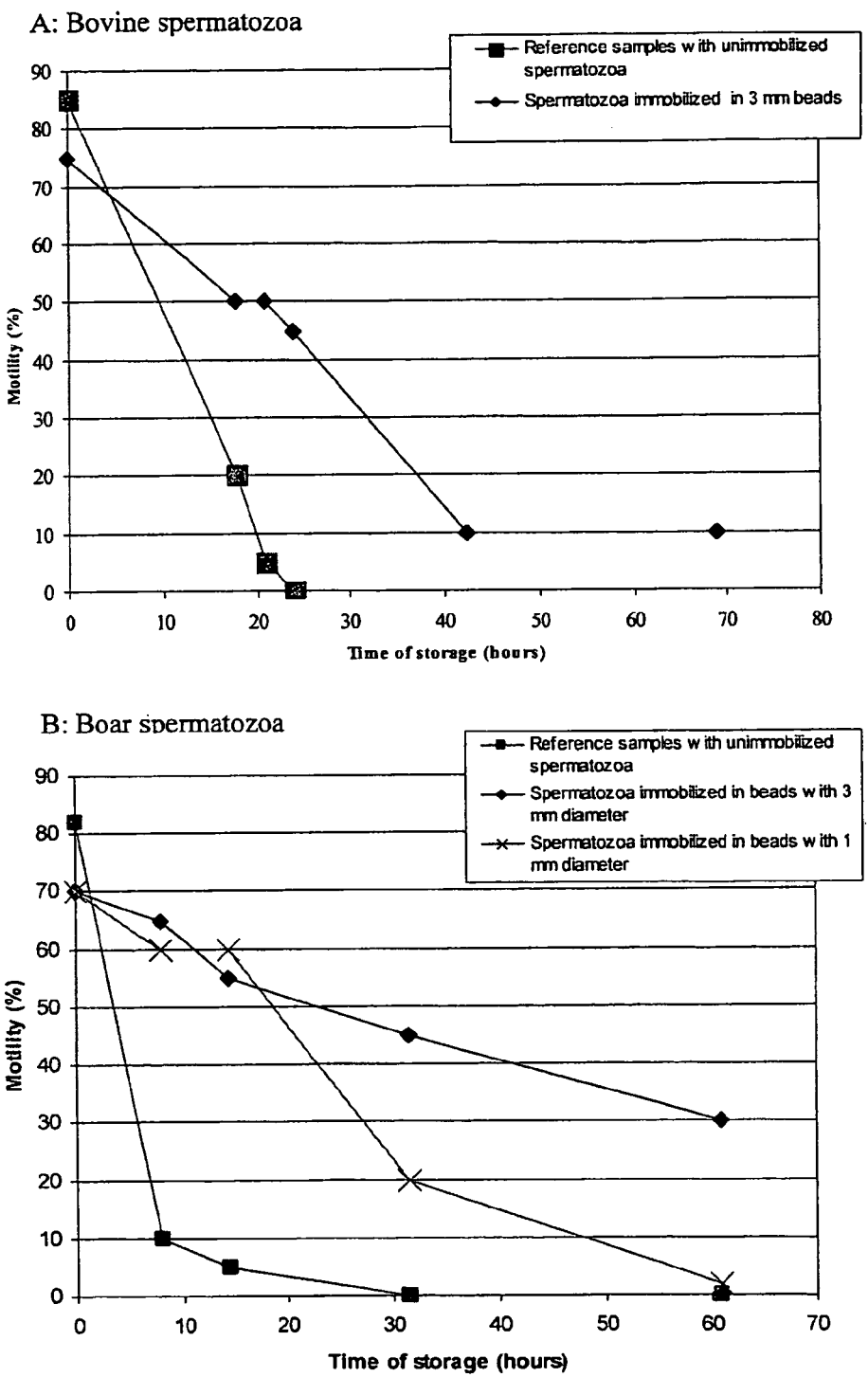
FIG. 2: shows in-vitro-storage of bovine spermatozoa (Pane A) and boar spermatozoa (Pane B) at 37° C. Values of motility are given as functions of time of storage in reference samples and samples with immobilized spermatozoa.
Figure 3:
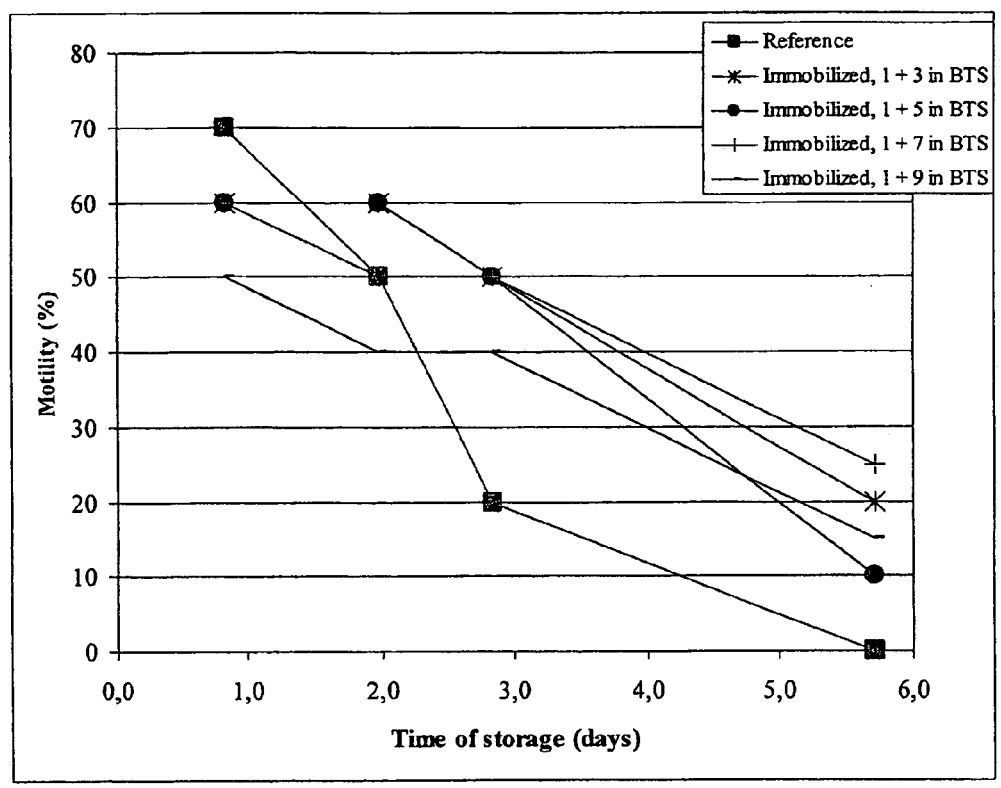
FIG. 3: shows in-vitro storage of boar spermatozoa at ambient temperatures (18° C.). Values of motility are given as functions of time of storage in reference samples and in samples with immobilized spermatozoa Different amount of storage medium relative to the amount of beads has been used in the storage experiments, as indicated in the series name. The spermatozoa are immobilized in beads with a diameter of 1 mm at a concentration of $1 \times 10^9$ spermatozoa/ml.

It must be kept in mind that the data presented in FIG. 2 are obtained using a artificial experimental system, which is not representative for the in-vivo situation within the female animal. The data presented in FIG. 2 does, however, indicate that both bovine and boar spermatozoa survive and can withhold motility for fairly long periods when being immobilized in a calcium alginate gel network even at physiological temperature. The data may also indicate that immobilization with calcium alginate gel networks can be used in order to sustain the motility of spermatozoa during storage at physiological temperatures. This may be especially important as the time of insemination is critical in order to obtain good fertilization results. The time of insemination is critical because the spermatozoa have a limited time of survival after insemination. The results may therefore indicate that immobilization of spermatozoa combined with a controlled release after insemination can be used in order to extend the time period from insemination to fertilization.

Insemination Trials

Insemination trials have been performed in a total of 9 sows in one herd. The sows were due for culling directly from weaning of the previous litter of piglets, but culling was postponed until approximately 4 weeks post insemination.

In the abattoir, reproductive organs were collected directly after evisceration and examined within 15 minutes. The number of corpora lutea in the ovaries and the number of embryos (if any) in the uterine horns were counted and recorded. By interfering at this early stage of pregnancy, the possibility of observing every embryo present (even degenerated) is relatively high. By observing the number of piglets born at full term one has a high risk of losing a high percentage of embryos, since any conceptus and embryo dead before ossification will be resorbed by the maternal system and no remnants will be visible at term. As much as 30% of fertilised swine ova may die and disappear from conception to ossification. In our trials, a good estimate of fertilisation rate can be calculated for each sow by counting the number of embryos and the number of corpora lutea at 4 weeks.

The timing of the inseminations varied from normal to one day earlier than normal, and both single and double inseminations have been performed. The results of these insemination trials are shown in table 1.

TABLE 1

Number of inseminated sows, pregnancy rate and fertilisation rate (in pregnant animals) with insemination trials.

| Method | # sows | Pregnant (%) | Fertilisation rate (%) |
|---|---|---|---|
| Imm. sperm, day $1^1$ + 2 | 5 | 4 (80%) | 57% |
| Re-dissolved imm. sperm day 1 + 2 | 4 | 2 (50%) | 66% |

[1]Day 1 = the day of spermatozoa collection

Insemination trials have also been performed with bovine spermatozoa. These trials are less easy to quantify as no large trial herds are available. These trials have been conducted in one herd with 20 available heifers. The heifers were estrus synchronized before insemination. Good fertilization rates have been achieved using immobilized bovine spermatozoa. In the study, 6 out of 12 heifers inseminated with immobilized spermatozoa stored 24 hours were fertilized, confirmed by pregnancy control.

The spermatozoa had been immobilized in alginate, stored immobilized at ambient temperature for different periods, inseminated dissolved or undissolved. The timing of the inseminations varied from normal to one day earlier than normal, and only single inseminations have been performed. Pregnant animals were confirmed by rectal examination 5-7 weeks post insemination. The results of these trials are shown in table 2.

TABLE 2

Insemination trials in cattle: Method used, number of inseminated heifers and pregnancy rate.

| Ins. Trial | Method | # heifers | Pregnant (%) |
|---|---|---|---|
| 1 | Sperm. imm., stored for 24 hours at 18° C., dissolved immediately before insemination | 12 | 6 (50%) |
| 2 | Sperm. imm., stored for 24 hours at 18° C., inseminated undissolved one day earlier than normal relative to estrus | 3 | 1 (33.3%) |
| 3 | Sperm. imm., stored for 48 hours at 18° C., dissolved immediately before insemination | 5 | 4 (80%) |

These data show that spermatozoa immobilized in calcium alginate beads not only maintain motility but also maintain all functional properties necessary for fertilization. Thus, Geno and Norsvin have demonstrated that spermatozoa immobilized in calcium alginate gel can be used for insemination, and cause can cause fertilization of both cattle and pigs.

Example 2

Energy Consumption of Immobilized Spermatozoa

Without being restricted to one specific theory, it is believed that immobilization of spermatozoa results in reduced energy consumption by the spermatozoa, and that this is beneficial as regards shelf life and their fertilization capacity.

Thus, to investigate this theory, bovine spermatozoa were immobilized in alginate beads at a concentration of approximately $150 \times 10^6$ spermatozoa/ml and added to 2 times the bead volume of milk dilution buffer. Reference samples with freely suspended spermatozoa were prepared from the same ejaculate containing the same total concentration of spermatozoa per total volume in milk dilution buffer. The samples were made anaerobic by a flushing with $N_2$ prior to storage at 20° C. Samples of the milk dilution buffer were taken during the storage period and the productions of lactate from the spermatozoa in the samples were measured by HPLC. The results are presented in table 3:

TABLE 3

Lactate production of immobilized and freely suspended spermatozoa during storage at ambient temperatures.

| Time of storage (days) | Immobilized spermatozoa | Reference samples |
|---|---|---|
| 1 | 4.21 | 16.1 |
| 2 | 6.00 | 20.6 |
| 3 | 6.90 | 22.1 |

The values are given as nanomoles of lactate produced per 350 mill spermatozoa.

Example 3

Immobilization of Semen from Silver Fox (Vulpes Vulpes)

Mixed semen of good quality from three adult silver fox (Vulpes vulpes) males was diluted in EDTA extender to 228× $10^6$ sperm cells per ml and transported to the laboratory. Three hours after collection and dilution, an aliquot of the semen was centrifuged at 2000 rpm for 10 min. The sediment was mixed with alginate (LF10/60) and beads were formed as described in this patent application. The beads were stored in modified Biladyl at 18° C. The remaining semen was stored in EDTA at 18° C. as control.

The beads were dissolved after 48 hours. Both the dissolved semen and the control semen were heated to 35° C. for 20 minutes before evaluation of motility as percent motile sperm was performed by phase microscopy at 10× and 25× magnification on a heating plate at 38° C.

TABLE 4

Motility of immobilised stored and not immobilised (control) silver fox semen.

|  | Motility on arrival | Motility after storage for 48 hrs |
|---|---|---|
| Control semen | 75% | 45-50% |
| Immobilized semen (after dissolved) |  | 55-60% |

Example 4

Piglets Born at Full Term after Single Intrauterine Insemination with Alginate Immobilised Boar Semen Mixed semen from 3 adult boars was treated according to the present invention and the beads were used for intrauterine insemination of a sow that later farrowed after full term pregnancy. The sow had been weaned from her previous litter on Feb. 8, 2007 and was inseminated with semen immobilized in alginate beads once on Feb. 12, 2007. The sow gave birth to 16 liveborn piglets on Jun. 10, 2007. There were no stillborn piglets in the litter and all piglets looked normal at clinical inspection.

Example 5

Immobilization of Ram Semen in Alginate

Semen from two AI rams was collected with an artificial vagina and brought to the lab within ten minutes. The semen was diluted 1+3 in a skimmed milk based extender (Curtis P G, Forteath A D, Polge C. Survival of bull sperm frozen in milk diluents containing varying concentrations of glycerol and fructose. Proc Ivth Int Congr Anim Reprod 1961; 3:952-956), before addition of alginate, and forming beads as described in patent application 0613288.0, example 1. The beads were stored in skimmed milk based extender at either 5° C. or ambient temperature. Immobilized spermatozoa were released from the beads before microscopic evaluation of motility as percent motile sperm cells 24 and 48 hours after immobilization. Due to practical reasons, controls were not included in this study. However, viability parameters including motility will be impaired during storage of liquid ram semen at 5° C. or 20° C. for 30 hours (Paulenz H, Soderquist L, Perez-Pe R, Berg K A. Effect of different extenders and storage temperatures on sperm viability of liquid ram semen. Theriogenology 2002: 57(2):823-36).

TABLE 5

Motility of immobilized ram semen stored at different temperatures for 24 hours and 48 hours.

|  | Storage temperature | Motility after 24 h storage | Motility after 48 h storage |
|---|---|---|---|
| Ram 1 | 5° C. | 75-85% | 70-80% |
|  | 20° C. | 70-80% | 65-75% |
| Ram 2 | 5° C. | 75-85% | 70-80% |
|  | 20° C. | 70-80% | 65-75% |

The invention claimed is:

1. Immobilized sperm cells, comprising one or more sperm cells embedded in a biopolymer particle, said biopolymer particle comprising alginate rich in guluronic acid arranged in a solid gel-network.

2. The immobilized sperm cell according to claim 1, wherein alginate is calcium alginate.

3. The immobilized sperm cell according to claim 1, wherein the alginate concentration is at least 0.1%.

4. The immobilized sperm cell according to claim 1, wherein the alginate concentration is between at least 0.1% and 6% alginate.

5. The immobilized sperm cell according to claim 4, wherein the alginate concentration is at least 1%.

6. The immobilized sperm cell according to claim 4, wherein the alginate concentration is at least 2%.

7. The immobilized sperm cell according to claim 4, wherein the alginate concentration is 6%.

8. The immobilized sperm cell according to claim 1, having a sperm cell concentration of at least $0.1 \times 10^6$ sperm cell/ml.

9. The immobilized sperm cell according to claim 8, having a sperm cell concentration of at least $100 \times 10^6$ sperm cell/ml.

10. The immobilized sperm cell according to claim 8, having a sperm cell concentration of at least $2.5 \times 10^9$ sperm cell/ml.

11. The immobilized sperm cell according to claim 1, wherein the particles are stored in a solution.

12. The immobilized sperm cell according to claim 11, wherein the storage solution: biopolymer particle ratio is at least between 1:1 and 1:100.

13. The immobilized sperm cell according to claim 1, wherein the one or more sperm cell are co-embedded with one or more antioxidants.

14. The immobilized sperm cell according to claim 13, wherein the antioxidant is selected form the group consisting of pyruvate, 2,2,6,6-tetrametylpeperidin-1-oxyl, 4-hydroksy-2,2,6,6-tetra-, metyl-peperidin-1-oxyl, superoxide-dismutase, catalase, glutathionperoxydase, butylated hydroxytoluen, butylated hydroxyanisol.

15. The immobilized sperm cell according to claim 1, wherein said particle is coated.

16. The immobilized sperm cell according to claim 15, wherein the coating is selected from the group consisting of polylysin, chitosan, cellulose sulphate, hydroxylpropylmethylcellulose or polydiallyldimethylammonium chloride.

17. The immobilized sperm cell according to claim 1, wherein the one or more sperm cell in addition is co-embedded with compounds or agents which are beneficial for fertilizing capacity and/or animal health.

18. The immobilized sperm cell according to claim 17, wherein the one or more sperm cell is co-embedded with one or more of the compounds or agents selected from the group consisting of extenders, cryoprotectants, antibiotics, antibodies, antioxidants, proteins, and hormones.

19. The immobilized sperm cell according to claim 1, wherein the one or more sperm cell originates from an animal selected form the group consisting of swine, cattle, horses, sheep, goats, rabbits, poultry, pets like pedigree dogs, fur animals, aquatic animals, and endangered animal species.

20. The immobilized sperm cell according to claim 19, wherein the one or more sperm cell are collected from an animal selected from the group consisting of swine, cattle, fur animals and horse.

21. The immobilized sperm cell according to claim 1, wherein the one or more sperm cell is contained in seminal fluid.

22. The immobilized sperm cell according to claim 1, wherein the particles are further treated by dehydration, cryopreservation or freeze-drying.

23. The immobilized sperm cell according to claim 1, wherein the particles are formed directly in a semen container.

* * * * *